United States Patent
Ehara et al.

(10) Patent No.: US 11,857,579 B2
(45) Date of Patent: Jan. 2, 2024

(54) COMPOSITION FOR PROMOTING THE SECRETION OF FGF21

(71) Applicant: MORINAGA MILK INDUSTRY CO., LTD., Tokyo (JP)

(72) Inventors: Tatsuya Ehara, Kanagawa (JP); Hirohisa Izumi, Kanagawa (JP); Takashi Shimizu, Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 16/980,692

(22) PCT Filed: Mar. 23, 2018

(86) PCT No.: PCT/JP2018/011917
§ 371 (c)(1),
(2) Date: Sep. 14, 2020

(87) PCT Pub. No.: WO2019/180964
PCT Pub. Date: Sep. 26, 2019

(65) Prior Publication Data
US 2021/0008129 A1  Jan. 14, 2021

(51) Int. Cl.
*A61K 35/745* (2015.01)
*A23L 33/135* (2016.01)
*A61K 31/7016* (2006.01)
*A61K 31/702* (2006.01)

(52) U.S. Cl.
CPC .......... *A61K 35/745* (2013.01); *A23L 33/135* (2016.08); *A61K 31/702* (2013.01); *A61K 31/7016* (2013.01); *A23V 2400/519* (2023.08)

(58) Field of Classification Search
None
See application file for complete search history.

(56) References Cited

U.S. PATENT DOCUMENTS

| | | | | |
|---|---|---|---|---|
| 7,993,903 B2* | 8/2011 | Hayakawa | ................ | A61P 3/06 435/252.1 |
| 8,497,114 B2* | 7/2013 | Kondo | ................ | C12N 1/205 424/93.4 |
| 9,456,629 B2* | 10/2016 | Hougee | ................ | A61K 31/702 |
| 2002/0015990 A1 | 2/2002 | Tomita et al. | | |
| 2010/0111915 A1* | 5/2010 | Isolauri | ................ | A61K 35/745 424/93.45 |
| 2010/0150890 A1 | 6/2010 | Beppu et al. | | |
| 2012/0269790 A1 | 10/2012 | Mellado et al. | | |

FOREIGN PATENT DOCUMENTS

| | | | |
|---|---|---|---|
| CN | 1696281 A | | 11/2005 |
| JP | 10-130160 A | | 5/1998 |
| JP | 10-175867 A | | 6/1998 |
| JP | 2013-505283 A | | 2/2013 |
| JP | 2017-203030 A | | 11/2017 |
| WO | WO2008/120712 A1 | | 10/2008 |
| WO | WO2010/071421 A1 | | 6/2010 |
| WO | WO2017/009187 A1 | | 1/2017 |
| WO | WO2017/145415 A1 | | 8/2017 |

OTHER PUBLICATIONS

Zhang et al. Journal of Functional Foods. 2017, 30, pp. 220-227.*
Chen et al. The Journal of Nutritional Biochemistry, 2018, vol. 54, pp. 87-94, published on line Nov. 2017, pp. 1-18.*
Kim Hayes, "5 Reasons You are always Cold", AARP publication on line on Feb. 2018, retrieved from webpage https://www.aarp.org.healht/conditions-treatemtns on Dec. 8, 2022, pp. 1-6.*
Sayama, K., et al., "Inhibitory Effect of Bifidobacterium on the Development of Arteriosclerosis in Mice," Japanese Journal of Lactic Acid Bacteria, 2011, vol. 22, No. 2, p. 138 (General Lecture 37) (Purpose, Results and Discussion), with English language translation thereof.
Lau, K. et al., "Bridging the Gap between Gut Microbial Dysbiosis and Cardiovascular Diseases," Nutrients, 2017, vol. 9 Iss.8, p. 859.
Liu, H.-X., et al., "Microbiota and bile acid profiles in retinoic acid-primed mice that exhibit accelerated liver regeneration," Oncotarget, 2015, vol. 7, No. 2. pp. 1096-1106.
Wang, H., et al., "Bifidobacteria may be benefical to intestinal microbiota and reduction of bacterial translocation in mice following ischaemia and reperfusion injury," Br. J. Nutr., 2013, vol. 109, pp. 1990-1998.
Itoh, N., et al., "Evolution of the Fgf and Fgfr gene families," Trends in Genetics 2004;20(11):563-569.
Ryden, M., "Fibroblast growth factor 21: an overview from a clinical perspective," Cell. Mol. Life Sci. 2009;66:2067-2073.
Kharitonenkov, A., et al., "The Metabolic State of Diabetic Monkeys Is Regulated by Fibroblast Growth Factor-21," Endocrinol. 2007;148(2):774-781.
Soberg, S., et al., "FGF21 Is a Sugar-Induced Hormone Associated with Sweet Intake and Preference in Humans," Cell Metabolism 2017;25(5):1045-1053.
Hondares, E., et al., "Hepatic FGF21 Expression Is Induced at Birth via PPARalpha in Response to Milk Intake and Contributes to Thermogenic Activation of Neonatal Brown Fat," Cell Metabolism 2010;11(3):206-212.
Tanajak, P., et al., "Effects of fibroblast growth factor 21 on the heart," J. Endocrinol. 2015;227:R13-R30.
Domouzoglou, E. M., et al., "Fibroblast growth factors in cardiovascular disease: The emerging role of FGF21," Am. J. Physiol. Heart Circ. Physiol. 2015;309(6):H1029-H1038.
Lin, Z, et al., "Fibroblast Growth Factor 21 Prevents Atherosclerosis by Suppression of Hepatic Sterol Regulatory Element-Binding Protein-2 and Induction of Adiponectin in Mice," Circulation 2015;131(21):1861-1871.

(Continued)

*Primary Examiner* — Vera Afremova
(74) *Attorney, Agent, or Firm* — Cermak Nakajima & McGowan LLP; Shelly Guest Cermak

(57) ABSTRACT

An object of the present invention is to provide a novel composition for promoting the secretion of FGF21. The object is achieved by a composition for promoting the secretion of FGF21, including a *Bifidobacterium* bacterium as an active ingredient.

7 Claims, No Drawings

Specification includes a Sequence Listing.

(56) References Cited

OTHER PUBLICATIONS

International Search Report for PCT Patent App. No. PCT/JP2018/011917 (dated Jun. 5, 2018).
Extended European Search Report for European Patent App. No. 18910930.9 (dated Oct. 6, 2021).
Ballester, M., et al., "Dietary intake of bioactive ingredients impacts liver and adipose tissue transcriptomes in a porcine model of prepubertal early obesity," Scientific Reports 2020;10(1):5375 (14 pp).
Gao, M., et al., "Hydrodynamic delivery of FGF21 gene alleviates obesity and fatty liver in mice fed a high-fat diet," J. Controlled Release 2014;185:1-11.
Li, X., et al., "FGF21 alleviates pulmonary hypertension by inhibiting mTORC1/EIF4EBP1 pathway via H19," Journal of Cellular and Molecular Medicine 2022;26(10):3005-3021.
Communication Pursurant to Article 94(3) EPC for European Patent App. No. 18910930.9 (dated Sep. 26, 2022).
Office Action from China National Intellectual Property Administration for Application No. 201880091708.9, (dated Mar. 4, 2023) with English translation.
Long, Xiaoxue et al., "Bifidobacterium adolescentis Alleviates Liver Steatosis and Steatohepatitis by Increasing Fibroblast Growth Factor 21 Sensitivity," (Dec. 30, 2021); Front. Endocrinol. vol. 12, Article 773340; pp. 1-12.
Dongmin, Lui, et al., "Advances in the study of tea and its polyphenolic compounds to modulate obesity and coexisting disorders," (2019); Genom. and Appl. Biol.; vol. 38, No. 12; pp. 5603-5615.
Shkoporov, A.N. et al., "Production of human basic fibroblast growth factor (FGF-2) in Bifidobacterium breve Using a neries of Novel expression/secretion vectors," Biotechnol Lett (2008); 30: pp. 1983-1988.

\* cited by examiner ially, the present invention relates to a composition
COMPOSITION FOR PROMOTING THE SECRETION OF FGF21

This application is a national phase entry under 35 U.S.C. § 371 of PCT Patent Application No. PCT/JP2018/011917, filed on Mar. 23, 2018, the entirety of which is incorporated by reference. Also, the Sequence Listing filed electronically herewith is hereby incorporated by reference (File name: 2020-09-14T 216-038 Seq List; File size: 574 bytes; Date recorded: Sep. 14, 2020).

TECHNICAL FIELD

The present invention relates to a composition for promoting the secretion of fibroblast growth factor 21 (FGF21). In particular, the present invention relates to a composition for promoting the secretion of fibroblast growth factor 21 (FGF21), containing a *Bifidobacterium* bacterium as an active ingredient.

BACKGROUND ART

FGF21 is a secretory polypeptide that belongs to a subfamily including FGF19, FGF21, and FGF23, of the fibroblast growth factor (FGF) (Non Patent Literature 1).

FGF21 is independent of heparin and functions as a hormone in regulation of the glucose metabolism, lipid metabolism, and energy metabolism.

It has been reported that the promotion of the secretion of FGF21 leads to acceleration of the lipid availability at the whole-body level, acceleration of the energy consumption, suppression of the triglyceride accumulation in the liver, induction of the fatty acid oxidation, and the like (Non Patent Literatures 2 and 3).

It is also reported that, when a subject takes sucrose, the FGF21 concentration in the serum rapidly increases and the FGF21 reduces the palatability of the subject to sucrose (Non Patent Literature 4).

It is also reported that, in the neonatal period, the body temperature increases with the increase in the FGF21 concentration in the serum and in the expression of FGF21 gene in the liver and that FGF21 is thus important for maintaining the body temperature in the neonatal period in which the hypothermia is likely to occur (Non Patent Literature 5).

It is also reported that FGF21 is important for protecting the cardiac function of a subject suffering from, for example, myocardial infarction, ischemia-reperfusion injury, cardiac hypertrophy, diabetic cardiomyopathy, or the like (Non Patent Literature 6).

It is also reported that, in the atherosclerosis, FGF21 protects a blood vessel from plaque formation by improving the vascular endothelium function (Non Patent Literatures 7 and 8).

On the other hand, it has been known that an effect for promoting the energy metabolism is exhibited in the body by administrating a lactic acid bacterium having productivity of 2,3-dihydro-3,5-dihydroxy-6-methyl-4H-pyran-4-one (Patent Literature 1).

However, it has not been known that the secretion of FGF21 in the body is promoted by administrating a *Bifidobacterium* bacterium.

CITATION LIST

Patent Literature

Patent Literature 1: WO2008/120712

Non-Patent Literature

Non Patent Literature 1: Itoh et al., Trends Genet., 20(11): 563-69 (2004)
Non Patent Literature 2: Ryden, M., et al., Cell. Mol. Life Sci., 66: 2067-2073 (2009)
Non Patent Literature 3: Kharitonenkov, A., et al., Endocrinology, 148: 774-781 (2007)
Non Patent Literature 4: Soberg S., et al., Cell Metab., 25(5): 1045-1053 (2017)
Non Patent Literature 5: Hondares E., et al., Cell Metab., 11(3): 206-12 (2010)
Non Patent Literature 6: Pongpan Tanajak, et al., J. Endocrinol., 227: R13-R30 (2015)
Non Patent Literature 7: Domouzoglou EM., Am. J. Physiol. Heart Circ. Physiol., 309(6): H1029-38 (2015)
Non Patent Literature 8: Lin Z., Circulation, 131 (21): 1861-71 (2015)

SUMMARY OF INVENTION

Technical Problem

An object of the present invention is to provide a novel composition for promoting the secretion of FGF21.

Solution to Problem

The present inventors have found that a *Bifidobacterium* bacterium has an action of promoting the secretion of FGF21 in a mammal that takes (including "has administered") the *Bifidobacterium* bacterium, completing the present invention.

Specifically, the present invention relates to a composition for promoting the secretion of FGF21, containing a *Bifidobacterium* bacterium as an active ingredient.

In a preferred embodiment, the composition for promoting the secretion of FGF21 is used for modulating palatability, maintaining body temperature, or protecting a blood vessel.

In a preferred embodiment, the composition for promoting the secretion of FGF21 is used for preventing or treating the unbalanced diet, sensitivity to cold, hypothermia, myocardial infarction, ischemia-reperfusion injury, cardiac hypertrophy, diabetic cardiomyopathy, arteriosclerosis, or vascular plaque formation.

In a preferred embodiment, the composition for promoting the secretion of FGF21 comprises a prebiotic.

In a preferred embodiment, the prebiotic in the composition for promoting the secretion of FGF21 is lactulose, raffinose, and galactooligosaccharide.

In a preferred embodiment, the *Bifidobacterium* bacterium in the composition for promoting the secretion of FGF21 is *Bifidobacterium* breve.

In a preferred embodiment, the *Bifidobacterium* breve in the composition for promoting the secretion of FGF21 is *Bifidobacterium* breve M-16V (NITE BP-02622).

In a preferred embodiment, the composition for promoting the secretion of FGF21 is a food or drink composition.

In a preferred embodiment, the composition for promoting the secretion of FGF21 is a pharmaceutical composition.

Another embodiment of the present invention is use of a *Bifidobacterium* bacterium for the manufacture of a composition for preventing or improving a disease, a symptom, a condition, or a disorder attributable to a failure of FGF21 production and/or a failure of FGF21 secretion.

Another embodiment of the present invention is a *Bifidobacterium* bacterium used for preventing or improving a disease, a symptom, a condition, or a disorder attributable to a failure of FGF21 production and/or a failure of FGF21 secretion.

Another embodiment of the present invention is use of a *Bifidobacterium* bacterium for preventing or improving a disease, a symptom, a condition, or a disorder attributable to a failure of FGF21 production and/or a failure of FGF21 secretion.

Another embodiment of the present invention is a method for preventing or improving a disease, a symptom, a condition, or a disorder attributable to a failure of FGF21 production and/or a failure of FGF21 secretion, the method comprising a step of administering a *Bifidobacterium* bacterium to a subject who has a need to prevent or improve a disease, a symptom, a condition, or a disorder attributable to a failure of FGF21 production and/or a failure of FGF21 secretion.

Advantageous Effects of Invention

According to the present invention, a novel composition for promoting the secretion of FGF21 can be provided.

DESCRIPTION OF EMBODIMENTS

The present invention will be described in detail below.

The composition for promoting the secretion of FGF21 of the present invention contains a *Bifidobacterium* bacterium as an active ingredient. Hereinafter, the bacterium is sometimes referred to as "this bacterium".

Note that the composition for promoting the secretion of FGF21 of the present invention includes a mixture regardless of whether the components of the composition for promoting the secretion of FGF21 are uniform or nonuniform.

This bacterium, which is an active ingredient of the composition for promoting the secretion of FGF21 of the present invention, has an action of promoting secretion of FGF21.

As used herein, the action of promoting the secretion of FGF21 means that, when a mammal takes (herein including "has administered") this bacterium, the amount of FGF21 secreted is larger than when the mammal does not take (herein including "not have administered") this bacterium.

In this situation, the larger amount of FGF21 secreted may be caused by a change from an off-state to an on-state of the expression of FGF21 gene, or may be caused by the promotion of the expression of FGF21 gene, or may be caused by the change from a state where the FGF21 gene is originally expressed but FGF21 is not secreted to a state where the FGF21 is secreted. The FGF21 gene is preferably the FGF21 gene in the liver. In addition, the larger amount of FGF21 secreted can be determined by, for example, measuring the FGF21 concentration in the serum.

Examples of mammals include human, cattle, sheep, goat, pig, dog, cat, and horse. The mammal is preferably a human. The mammal is herein sometimes referred to as a "subject".

The *Bifidobacterium* bacterium in the present invention is a gram-positive strictly anaerobic bacterium.

The *Bifidobacterium* bacterium is not limited as long as the bacterium can promote the secretion of FGF21 when a mammal takes the bacterium. For example, *Bifidobacterium longum* subsp. *longum, Bifidobacterium lactis, Bifidobacterium animalis, Bifidobacterium breve, Bifidobacterium longum* subsp. *infantis*, and *Bifidobacterium adolescentis* can be used. Note that the *Bifidobacterium longum* subsp. *longum* is sometimes simply abbreviated as *Bifidobacterium longum*. In addition, *Bifidobacterium longum* subsp. *infantis* is sometimes simply abbreviated as *Bifidobacterium infantis*.

In the present invention, *Bifidobacterium breve, Bifidobacterium longum* subsp. *longum*, and *Bifidobacterium longum* subsp. *infantis* are preferred.

Among them, *Bifidobacterium breve* FERM BP-11175, *Bifidobacterium breve* M-16V (NITE BP-02622), *Bifidobacterium longum* subsp. *longum* BB536 (NITE BP-02621), and *Bifidobacterium longum* subsp. *infantis* M-63 (NITE BP-02623) are more preferred.

The bacterium given the accession number of FERM BP-11175 has been deposited under the Budapest Treaty with an international depository authority, the International Patent Organism Depositary of the National Institute of Advanced Industrial Science and Technology (current name: the Biological Resource Center of the National Institute of Technology and Evaluation, Room 120, 2-5-8, Kazusakamatari, Kisarazu, Chiba, 292-0818 JAPAN) on Aug. 25, 2009.

The bacterium given the accession number of NITE BP-02622 has been deposited under the Budapest Treaty with an international depository authority, the NITE Patent Microorganisms Depositary of the Biological Resource Center of the National Institute of Technology and Evaluation (Room 122, 2-5-8, Kazusakamatari, Kisarazu, Chiba, 292-0818 JAPAN) under the accession number of NITE BP-02622 on Jan. 26, 2018.

The bacterium given the accession number NITE BP-02621 has been deposited under the Budapest Treaty with an international depository authority, the NITE Patent Microorganisms Depositary of the Biological Resource Center of the National Institute of Technology and Evaluation (Room 122, 2-5-8, Kazusakamatari, Kisarazu, Chiba, 292-0818 JAPAN) under the accession number of NITE BP-02621 on Jan. 26, 2018.

The bacterium given the accession number of NITE BP-02623 has been deposited under the Budapest Treaty with an international depository authority, the NITE Patent Microorganisms Depositary of the Biological Resource Center of the National Institute of Technology and Evaluation (Room 122, 2-5-8, Kazusakamatari, Kisarazu, Chiba, 292-0818 JAPAN) under the accession number of NITE BP-02623 on Jan. 26, 2018.

The *Bifidobacterium* bacterium of the present invention is not limited to the deposited bacteria and may be a bacterium that is substantially equivalent to any of the deposited bacteria. A bacterium that is substantially equivalent to a deposited bacterium means a bacterium that belongs to the same genus or the same species as the deposited bacterium, that can promote the secretion of FGF21 in a mammal when the mammal takes the bacterium, and that has a base sequence of the 16S rRNA gene having a homology of not less than 98%, preferably not less than 99%, more preferably 100% to the base sequence of the 16S rRNA gene of the deposited bacterium, and that preferably has, in addition to such a homology, the same microbiological characteristics as the deposited bacterium. In addition, the *Bifidobacterium* bacterium of the present invention may be a bacterium bred from any of the deposited bacteria or a bacterium substantially equivalent to any of the deposited bacteria through a variation treatment, gene recombination, screening of a natural variant, or the like as long as the effect of the present invention is not impaired.

This bacterium may be bacterial cells or may be a culture containing bacterial cells. In addition, the bacterium may be viable cells, killed cells, or both of viable cells and killed cells, but the bacterium is preferably viable cells. As long as the effect of the present invention is not impaired, lyophilization or various other operations may be additionally performed after culturing. The additional operation preferably provides a high survival of the viable cells.

This bacterium can be easily obtained by, for example, culturing the bacterium. The method of culture is not particularly limited as long as this bacterium can grow, and any method usually used for culture of a *Bifidobacterium* bacterium (*Bifidobacterium*) can be used with appropriate modification as required. For example, the temperature in culture is 25 to 50° C. and preferably 35 to 40° C. The culture may be performed under an aerobic condition or under an anaerobic condition, but preferably under an anaerobic condition. For example, the culture may be conducted under flow of an anaerobic gas, such as carbon dioxide gas. The culture may be conducted under a microaerophilic condition, such as in a liquid stationary culture.

The medium for culturing this bacterium is not particularly limited, and a medium usually used for culture of a *Bifidobacterium* bacterium can be used with appropriate modification as required. Specifically, as a carbon source, for example, a saccharide, such as galactose, glucose, fructose, mannose, cellobiose, maltose, lactose, sucrose, trehalose, starch, starch hydrolysate, or molasses can be used according to the assimilation. As a nitrogen source, for example, ammonia, or an ammonium salt or nitrate salt, such as ammonium sulfate, ammonium chloride, or ammonium nitrate, can be used. As an inorganic salt, for example, sodium chloride, potassium chloride, potassium phosphate, magnesium sulfate, calcium chloride, calcium nitrate, manganese chloride, or ferrous sulfate can be used. In addition, an organic component, such as peptone, soybean powder, defatted soybean meal, a meat extract, or yeast extract, may be used. As a prepared medium, for example, an MRS medium may be suitably used.

The composition for promoting the secretion of FGF21 of the present invention preferably contains a prebiotic. Prebiotics are digestion-resistant food components that have an advantageous effect on a host by selectively changing the proliferation and activity of a specific bacterium in the large intestine, thus improving the health of the host.

The prebiotic is not particularly limited as long as the prebiotic can promote the secretion of FGF21 when a mammal takes the prebiotic together with this bacterium, but, for example, lactulose, raffinose, galactooligosaccharide, fructooligosaccharide, soybean oligosaccharide, NYUKA OLIGO, xylooligosaccharide, isomaltooligosaccharide, coffee bean mannooligosaccharide, gluconic acid, polydextrose, and inulin are preferred, and lactulose, raffinose, and galactooligosaccharide are more preferred.

Lactulose is a disaccharide composed of fructose and galactose (4-O-β-D-galactopyranosyl-D-fructose, Gal β1-4 Fru) and can be produced by a known method, for example, methods described in JP-A-3-169888 and JP-A-6-228179. A commercially available lactulose (for example, manufactured by Morinaga Milk Industry Co., Ltd.) can also be used as the lactulose.

Raffinose is a trisaccharide in which one molecule each of fructose, galactose, and glucose are connected (β-D-fructofuranosyl-α-D-galactopyranosyl-(1-6)-α-D-glucopyranoside, Gal α1-6 Glc α1-2β Fru) and can be produced by a known method, for example, a method described in "Shokuhin Sin-sozai Yuko Riyo Gijutu Series (Series of technique for effective use of new materials for food) No. 6, "raffinose", page 2, Japan Confectionery and Innovative Food Ingredients Research Center, 1996". A commercially available raffinose (for example, manufactured by Nippon Beet Sugar Manufacturing Co., Ltd.) can also be used as the raffinose.

Galactooligosaccharide (GOS) is an oligosaccharide having a structure represented by Gal-(Gal)n-Glc (n is 1 to 3, β-1,4 bond or β-1,6 bond) or a mixture thereof. Galactooligosaccharide is industrially produced from lactose as a starting material through a transfer reaction with β-galactosidase and the main component thereof is 4'-galactosyllactose (4'-GL) which is a trisaccharide in which one molecule of galactose is connected to the non-reducing terminal of lactose. A commercially available galactooligosaccharide (for example, manufactured by Yakult Pharmaceutical Industry Co., Ltd.) can also be used as the galactooligosaccharide. One kind of galactooligosaccharide may be used or a mixture of two or more kinds thereof may be used.

The composition for promoting the secretion of FGF21 of the present invention enhances the FGF21-mediated function (activity) in a mammal that took the composition by promoting the secretion of FGF21 in the mammal. Accordingly, the composition for promoting the secretion of FGF21 of the present invention can be used for enhancing the FGF21-mediated function (activity).

Examples of the functions (activities) include modulation of palatability, maintenance of body temperature, and protection of a blood vessel. Thus, the composition for promoting the secretion of FGF21 of the present invention is preferably used for modulating palatability, maintaining body temperature, or protecting a blood vessel, for example.

Note that the use of the composition for promoting the secretion of FGF21 of the present invention may be a therapeutic use or a nontherapeutic use. Note that the "nontherapeutic" means not practiced within a medical practice, that is, a treatment practiced on a human body by a therapy.

It is known that FGF21 is involved in modulation of palatability of diet or palatability of the taste thereof (Non Patent Literature 4). The palatability of the diet or palatability of the taste is expected to be adjusted by taking the composition for promoting the secretion of FGF21 of the present invention. The diet includes a food and a drink, such as alcohol. The taste includes sweetness, saltiness, sourness, bitterness, and umami.

The modulation of palatability includes enhancement and suppression of palatability. Enhancement of palatability means that, when a mammal takes this bacterium, the palatability of diet or the palatability of taste is enhanced as compared with when the mammal does not take the bacterium. On the other hand, suppression of palatability means that, when a mammal takes this bacterium, the palatability of diet or the palatability of taste is suppressed as compared with when the mammal does not take the bacterium.

With modulation of the palatability, for example, unbalanced types of diet taken by a mammal are reduced so that the mammal can take a wide variety of types of diet without faddiness and the sense of taste is also adjusted. The modulation of palatability herein include the cases where 1) the faddiness due to the unbalanced diet is reduced, 2) the palatability deviated to sweetness is suppressed, 3) the intake of sugar and artificial sweetener is suppressed, 4) the diet with strong bitterness or strong sourness becomes able to be taken, 5) the palatability to saltiness is suppressed so that low salt foods becomes to be preferred, and 6) the palatability to alcohol is suppressed.

The diet taken by a mammal in the present invention may be not only a food or drink but also a specific component. Thus, the unbalanced types of diet taken by a mammal means a high intake of a specific food or drink or a specific component.

The food or drink is not particularly limited. In addition, an example of the specific component is a sweet component. The sweet components include carbohydrate-based sweet components and non-carbohydrate-based sweet components.

Examples of carbohydrate-based sweet components include a saccharide and a sugar alcohol.

The saccharide may be a monosaccharide, a disaccharide, a tri- or higher saccharide and examples thereof include glucose, maltose, fructose, trehalose, lactose, fructooligosaccharide, galactooligosaccharide, xylooligosaccharide, NYUKA OLIGO (registered tradename), soybean oligosaccharide, and isomaltooligosaccharide. The saccharide may also be a starch syrup which is a mixture of monosaccharides, isomerized sugars, or the like.

Examples of sugar alcohols include sorbitol, mannitol, maltitol, xylitol, erythritol, and reduced palatinose. The sugar alcohol may also be a reduced starch syrup which is obtained by reducing a starch syrup which is a mixture of monosaccharides.

Non-carbohydrate-based sweet components include non-carbohydrate-based natural sweet components and non-carbohydrate-based artificial sweet components.

Examples of non-carbohydrate-based natural sweet components include stevia and glycyrrhizin.

Examples of non-carbohydrate-based artificial sweet components include saccharin, aspartame, acesulfame K, and sucralose.

The maintenance of body temperature herein refers to maintenance of body temperature to prevent a state that has a trend toward a low body temperature state by increasing the body temperature.

The maintenance of body temperature to prevent a state that has a trend toward a low body temperature state by increasing the body temperature specifically means that, when there is a trend toward a low body temperature if a mammal does not take this bacterium, the decrease in the body temperature is prevented by taking this bacterium to prevent the low body temperature. The low body temperature state refers to a state where the body temperature taken under the arm is preferably 36.5° C. or lower, more preferably 36.0° C. or lower, further preferably 35.5° C. or lower, furthermore preferably 35.0° C. or lower, or a state where the core body temperature is 35.0° C. or lower.

The age of the mammal when the composition for promoting the secretion of FGF21 of the present invention is used for maintaining body temperature is not particularly limited, but the mammal is preferably an infant. In the present invention, the "infant" refers to a period from birth to about one-year old when the mammal is a human. Note that the infant of a human approximately corresponds to a mouse from birth to about 4-weeks old (the last day of the fourth week).

An example of protection of a blood vessel is the suppression of plaque formation in the blood vessel. An example of plaque is a plaque in arteriosclerosis. An example of arteriosclerosis is atheroma arteriosclerosis. An example of a blood vessel is a cardiac blood vessel.

In addition, the composition for promoting the secretion of FGF21 of the present invention can be used in a mammal for preventing or treating a disease, a symptom, a condition, a disorder, or the like that can be prevented or treated by promoting the secretion of FGF21. The "treatment" includes improvement.

Since the FGF21 secretion-promoting action in the present invention may be caused by a change from an off-state to an on-state of the expression of FGF21 gene, may be caused by the promotion of the expression of FGF21 gene, or may be caused by a change from a state where the FGF21 gene is originally expressed but FGF21 is not secreted to a state where the FGF21 is secreted as described above, the diseases, symptoms, conditions, disorders, or the like that can be prevented or treated by promoting the secretion of FGF21 include a disease, a symptom, a condition, a disorder, or the like that is caused by a failure of FGF21 production and/or a failure of FGF21 secretion. The failure of secretion includes a reduction in secretion.

Examples of such diseases, symptoms, conditions, or disorders include unbalanced diet, sensitivity to cold, hypothermia, myocardial infarction, ischemia-reperfusion injury, cardiac hypertrophy, diabetic cardiomyopathy, arteriosclerosis, and vascular plaque formation.

The composition for promoting the secretion of FGF21 of the present invention can be used as a food or drink composition, a pharmaceutical composition, or a feed composition. For example, a food or drink composition for promoting the secretion of FGF21, a pharmaceutical composition for promoting the secretion of FGF21, and a feed composition for promoting the secretion of FGF21 can be provided.

The food or drink composition for promoting the secretion of FGF21 of the present invention is not particularly limited as long as the composition contains this bacterium. The food or drink composition may be a food or drink of any form, such as liquid, paste, gelled solid, or powder. Examples of food or drink compositions include, in addition to tablet candies, fluid foods, and the like: wheat flour products, such as bread, macaroni, spaghetti, noodles, cake mixes, deep frying flour, bread crumps; instant foods, such as instant noodles, cup noodles, retort cooked foods, canned cooked foods, foods for microwave heating, instant soups and stews, instant miso soups and clear soups, canned soups, freeze-dried foods, and other instant foods; processed agricultural foods, such as canned agricultural foods, canned fruits, jams and marmalades, pickles, cooked beans, dried agricultural foods, and cereals (processed grain foods); processed marine product, such as canned marine foods, fish meat hams and sausages, kneaded marine products, marine dainties, and Tukudani (foods boiled in soy); processed stock farm products, such as canned stock farm foods and pastes and stock farm meat hams and sausages; milks and dairy products, such as processed milk, milk drinks, yogurts, lactic acid bacteria drinks, cheeses, ice creams, milk formula, creams, and other dairy products; oils and fats, such as butter, margarines, and vegetable oils; basic seasonings, such as soy sauce, miso, sauces, processed tomato seasonings, Mirins, and vinegars; compounded seasonings or foods, such as seasoning mixes, curry rouxes, dipping sauces, dressings, noodle soup bases, spices, and other compounded seasonings; frozen foods, such as frozen material foods, frozen semi-cooked foods, and frozen cooked foods; confectionary foods, such as caramels, candies, gummi candies, chewing gums, chocolates, cookies, biscuits, cakes, pies, snacks, crackers, Japanese cakes, rice cakes, bean sweets, dessert sweets, jellies, and other sweets; favorite drinks, such as carbonated drinks, natural fruit juices, fruit juice drinks, soft drinks with fruit juice, fruit pulp drinks, fruit drinks with fruit granules, vegetable drinks, soy milk, soy milk drinks, coffee drinks, tea drinks, powder drinks, concentrated drinks, sport drinks, nutrient drinks, alcohol drinks, and other favorite drinks; other commercially available foods, such as baby foods, Furikake (rice seasonings), and Ochazuke Nori (dried seasonings for rice in tea); infant formula; enteral nutritive foods; foods for special dietary uses, foods with health claims (foods for specified health uses, foods with nutrient function claims, foods with function claims); and nutritional supplement foods.

The food or drink composition may be a supplement, for example, a tablet supplement. When the composition is a supplement, this bacterium can be taken with no effect of other foods in terms of the daily food intake and the calorie intake.

The food or drink composition for promoting the secretion of FGF21 of the present invention can be produced by adding this bacterium to raw materials of a general food or drink, that is, the composition can be produced in the same manner as a general food or drink except for adding this bacterium. This bacterium can be added in any stage in the production process of the food or drink composition. The food or drink composition may be produced through a fermentation step using this bacterium added. Examples of such food or drink compositions include lactic acid bacterium drinks and fermented milks.

As raw materials of the food or drink composition, raw materials used in a general food or drink can be used. The food or drink composition produced can be orally taken.

The food or drink compositions for promoting the secretion of FGF21 the present invention include raw materials for producing a food or drink composition and components that are added to the food or drink composition during and after the production process of the food or drink composition, such as food additives. For example, this bacterium can be used as a starter for production of a fermented milk. Alternatively, this bacterium can be subsequently added to a fermented milk produced.

In the food or drink composition for promoting the secretion of FGF21 of the present invention, the content of this bacterium is appropriately set according to the aspect of the food or drink composition, and this bacterium is typically present in an amount in total preferably in the range of $1 \times 10^4$ to $1 \times 10^{13}$ cfu/g or $1 \times 10^4$ to $1 \times 10^{13}$ cfu/ml, more preferably in the range of $1 \times 10^5$ to $1 \times 10^{12}$ cfu/g or $1 \times 10^5$ to $1 \times 10^{12}$ cfu/ml, further preferably in the range of $1 \times 10^6$ to $1 \times 10^{11}$ cfu/g or $1 \times 10^6$ to $1 \times 10^{11}$ cfu/ml in the food or drink composition. The "cfu" represents the colony forming unit. When this bacterium is killed cells, cfu/g or cfu/ml can be replaced by (cells)/g or (cells)/ml.

When the food or drink composition for promoting the secretion of FGF21 of the present invention contains a prebiotic, it is preferred that the total amount of this bacterium is $1 \times 10^6$ to $1 \times 10^{12}$ cfu per gram of the total amount of the prebiotic, preferably $1 \times 10^7$ to $1 \times 10^{12}$ cfu, more preferably $1 \times 10^8$ to $1 \times 10^{12}$ cfu.

When the prebiotic is lactulose, raffinose, and galactooligosaccharide, it is preferred that the ratio by weight thereof is preferably 1 to 9:1 to 9:1 to 9, preferably 2 to 8:2 to 8:2 to 8, more preferably 3 to 7:3 to 7:3 to 7.

The food or drink composition for promoting the secretion of FGF21 of the present invention may be taken alone or may be taken together with another food or drink composition, a food or drink, a pharmaceutical composition, or a pharmaceutical. The food or drink composition for promoting the secretion of FGF21 of the present invention may be taken together with, for example: another food or drink composition, a food or drink, a pharmaceutical composition, or a pharmaceutical for promoting the secretion of FGF21; a food or drink composition, food or drink, pharmaceutical composition, or pharmaceutical for modulating palatability, maintaining body temperature, or protecting a blood vessel by promoting the secretion of FGF21 in a mammal; a food or drink composition, food or drink, pharmaceutical composition, or pharmaceutical for preventing or treating a disease, a symptom, a condition, or a disorder that can be prevented or treated by promoting the secretion of FGF21; or the like.

The food or drink composition for promoting the secretion of FGF21 of the present invention can be sold as a food or drink composition or a food or drink on which the application that is the promotion of FGF21 secretion is indicated. The food or drink composition for promoting the secretion of FGF21 of the present invention can also be sold as a food or drink composition or a food or drink on which the application that is the modulation of palatability, maintenance of body temperature, or protection of a blood vessel by promoting the secretion of FGF21 in a mammal is indicated. The food or drink composition for promoting the secretion of FGF21 of the present invention can also be sold as a food or drink composition or a food or drink on which the application that is the prevention or treatment of a disease, a symptom, a condition, a disorder, or the like that can be prevented or treated by promoting the secretion of FGF21 is indicated. Besides the above, any wording that represents an effect that secondarily arises by promoting the secretion of FGF21 can be used, of course.

In addition, the food or drink composition for promoting the secretion of FGF21 of the present invention can be provided or sold as a food or drink composition or a food or drink on which the application as a probiotic or the like (including health use) is indicated. The food or drink composition can also be provided or sold with an indication of, for example, "a person who desires a life with Bifidobacterium", "a person who wants to improve the intestinal environment", "a person who wants to condition the stomach", "a person who wants to make a good intestinal environment", "a person who wants to warm the body", "a person who wants to correct food faddiness", "a person who wants to improve the blood vessel function", "a person who wants to improve the blood flow", and the like as the subject to take the food or drink composition or the food or drink.

The "indication" means all acts to inform the consumers of such an application as above. All indications that evoke or suggest the application fall into the "indication" of the present invention regardless of the object, content, subject, medium, and the like of the indication, but the indication is preferably made by an expression that allows a consumer to directly recognize the application.

Specific examples of such acts of indication include: an act of writing the application on a commercial product regarding the food or drink composition for promoting the secretion of FGF21 or food or drink for promoting the secretion of FGF21 of the present invention or on a package thereof; an act of assigning, delivering, displaying for the purpose of assignment or delivery, or importing a commercial product with the applications written thereon or on the package thereof; an act of displaying or distributing an advertisement material, price list, or transaction document with respect to a commercial product with the applications written thereon, or of providing information of such an advertisement material, price list, or transaction document with the applications included therein by an electromagnetic method (the Internet, etc.). The indication is particularly preferably put on a package, a container, a catalog, a pamphlet, an advertisement material in the marketing site, such as POP, other documents, or the like.

In addition, the indication is preferably an indication approved by the government or the like (for example, an indication approved under various institutions established by the government and put in a manner based on the approval). Examples of indications include indications of a food with health claims or the like, more specifically, indications of a food with health claims, a health food, a functional food, an enteral nutritive food, a food for special dietary uses, a food with nutrient function claims, a quasi-drug, and the like. Besides, indications approved by the Consumer Affairs Agency, such as indications of a food for specified health uses, a food with nutrient function claims, and a food with function claims, and indications approved by the institution similar thereto are mentioned. Examples of the latter indications include an indication of a food for specified health uses, an indication of a conditional food for specified health uses, an indication that the product may influence the body structure or function, an indication about reduction of a disease risk, an indication about a function based on a scientific ground. More specific examples include an indication of a food for specified health uses (especially an indication of a health use) established in the Cabinet Office Ordinance on Approval, etc. of Indication of Special Use provided in the Health Promotion Act (Cabinet Office Ordinance No. 57 dated on Aug. 31, 2009) and similar indications thereto.

The pharmaceutical composition for promoting the secretion of FGF21 of the present invention is not particularly limited as long as the composition contains this bacterium. In the pharmaceutical composition for promoting the secretion of FGF21 of the present invention, this bacterium may be used as it is or may be used as a formulation prepared by mixing this bacterium with a physiologically-acceptable liquid or solid carrier for formulation.

The dosage form of the pharmaceutical composition for promoting the secretion of FGF21 of the present invention is not particularly limited. Specific examples include forms of tablet, pill, powder, liquid, suspension, emulsion, granule, capsule, syrup, suppository, injection, ointment, patch, eye drops, and nasal drops. In preparation into a formulation, a generally used additive, such as an excipient, a binder, a disintegrator, a lubricant, a stabilizer, a corrigent, a diluent, a surfactant, or an injection solvent, can be used as the carrier for formulation.

In addition, as the carrier for a formulation, various organic or inorganic carriers can be used according to the dosage form. Examples of carriers in the case of a solid formulation include an excipient, a binder, a disintegrator, a lubricant, a stabilizer, and a corrigent.

Examples of excipients include: sugar derivatives, such as lactose, sucrose, glucose, mannitol, and sorbitol; starch derivatives, such as corn starch, potato starch, a-starch, dextrin, and carboxymethyl starch; cellulose derivatives, such as crystalline cellulose, hydroxypropylcellulose, hydroxypropylmethylcellulose, carboxymethylcellulose, and carboxymethylcellulose calcium; Arabic rubber; dextran; pullulan; silicate derivatives, such as light anhydrous silicic acid, synthetic aluminum silicate, and magnesium aluminometasilicate; a phosphate derivative, such as calcium phosphate; a carbonate derivative, such as calcium carbonate; and a sulfate derivative, such as calcium sulfate.

Examples of binders include, in addition to the above excipients: gelatin; polyvinylpyrrolidone; and macrogol.

Examples of disintegrators include, in addition to the above excipients, chemically-modified starch or cellulose derivatives, such as croscarmellose sodium, carboxymethylstarch sodium, and crosslinked polyvinyl pyrrolidone.

Examples of lubricants include: talc; stearic acid; metal stearates, such as calcium stearate and magnesium stearate; colloidal silica; waxes, such as Peegum and spermaceti; boric acid; glycols; carboxylic acids, such as fumaric acid and adipic acid; a sodium carboxylate, such as sodium benzoate; a sulfuric acid salt, such as sodium sulfate; Leucine; lauryl sulfate salts, such as sodium lauryl sulfate and magnesium lauryl sulfate; silicic acid compounds, such as silicic anhydride and silicic acid hydrate; and starch derivatives.

Examples of stabilizers include: p-hyroxybenzoic acid esters, such as methylparaben and propylparaben; alcohols, such as chlorobutanol, benzyl alcohol, and phenylethyl alcohol; benzalkonium chloride; acetic anhydride; and sorbic acid.

Examples of corrigents include a sweetener, an acidulant, and a fragrance.

Note that examples of carriers used in the case of liquid agents for oral administration include a solvent, such as water, and a corrigent.

The amount of this bacterium in the pharmaceutical composition for promoting the secretion of FGF21 of the present invention is appropriately set according to the dosage form, the usage, the age and sex of the subject, the type of the disease, symptom, condition, or disorder, the degree thereof, other conditions, and the like, and a normal and preferred range thereof are the same as those in the food or drink composition for promoting the secretion of FGF21 of the present invention. When the pharmaceutical composition for promoting the secretion of FGF21 of the present invention contains a prebiotic, the total amount of this bacterium per gram of the total amount of the prebiotic is the same as in the food or drink composition for promoting the secretion of FGF21 of the present invention. When the prebiotic is lactulose, raffinose, and galactooligosaccharide, the ratio by weight thereof is the same as in the food or drink composition for promoting the secretion of FGF21 of the present invention.

The time of administration of the pharmaceutical composition for promoting the secretion of FGF21 of the present invention is not particularly limited and the time of administration can be appropriately selected according to the method for preventing or treating the disease, symptom, condition, or disorder to be addressed. The composition may be prophylactically administered or may be used in a maintenance therapy. The administration form is preferably determined according to the dosage form, the age, sex, and other conditions of the patient, the degrees of conditions of the patient, and the like. Note that the pharmaceutical composition for promoting the secretion of FGF21 of the present invention can be administered once a day or multiple times a day, or may be administered once every few days or once every few weeks.

The pharmaceutical composition for promoting the secretion of FGF21 of the present invention may be administered alone or may be administered together with another pharmaceutical composition, a pharmaceutical, a food or drink composition, or a food or drink. For example, the pharmaceutical composition for promoting the secretion of FGF21 of the present invention may be taken together with another pharmaceutical composition, a pharmaceutical, a food or drink composition, or a food or drink for promoting the secretion of FGF21; a pharmaceutical composition, pharmaceutical, food or drink composition, or food or drink for modulating palatability, maintaining body temperature, or protecting a blood vessel by promoting the secretion of FGF21 in a mammal; a pharmaceutical composition, pharmaceutical, food or drink composition, or food or drink for preventing or treating a disease, a symptom, a condition, a disorder, or the like that can be prevented or treated by promoting the secretion of FGF21; or the like.

Examples of the feed compositions for promoting the secretion of FGF21 of the present invention include a pet food, a feed for livestock, and a feed for cultured fish. The feed composition for promoting the secretion of FGF21 of the present invention can be produced by mixing this bacterium into a general feed or a raw material thereof, for example, a grain, lee, bran, fish powder, bone meal, oil or fat, skim milk powder, whey, mineral feed, or yeast. In addition, a feed composition may be produced through a fermentation step using this bacterium added, for example, as in silage. The produced feed composition can be orally administered to a general mammal, livestock, cultured fish, pet, and the like.

The content of this bacterium in the feed composition for promoting the secretion of FGF21 of the present invention is appropriately set according to the aspect of the feed composition and the administration subject thereof. The normal range and preferred range thereof are the same as those in the food or drink composition for promoting the secretion of FGF21 of the present invention. When the feed composition for promoting the secretion of FGF21 of the present invention contains a prebiotic, the total amount of this bacterium per gram of the total amount of the prebiotic is the same as that in the food or drink composition for promoting the secretion of FGF21 of the present invention. When the prebiotic is lactulose, raffinose, and galactooligosaccharide, the ratio by weight thereof is the same as that in the food or drink composition for promoting the secretion of FGF21 of the present invention.

Another embodiment of the present invention is use of a *Bifidobacterium* bacterium for the manufacture of a composition for promoting the secretion of FGF21.

Another embodiment of the present invention is a *Bifidobacterium* bacterium used for promoting the secretion of FGF21.

Another embodiment of the present invention is use of a *Bifidobacterium* bacterium for promoting the secretion of FGF21.

Another embodiment of the present invention is a method for promoting the secretion of FGF21, the method including a step of administering a *Bifidobacterium* bacterium to a mammal or a step of administering the composition for promoting the secretion of FGF21 of the present invention to a mammal.

Another embodiment of the present invention is a method of preventing or treating a disease, a symptom, a condition, a disorder, or the like that can be prevented or treated by promoting the secretion of FGF21, the method including a step of administering a *Bifidobacterium* bacterium to a mammal or a step of administering the composition for promoting the secretion of FGF21 of the present invention to a mammal.

Another embodiment of the present invention is use of a *Bifidobacterium* bacterium for the manufacture of a pharmaceutical composition, a food or drink composition, or a feed composition for modulating palatability, maintaining body temperature, or protecting a blood vessel.

Another embodiment of the present invention is a *Bifidobacterium* bacterium used for modulating palatability, maintaining body temperature, or protecting a blood vessel.

Another embodiment of the present invention is use of a *Bifidobacterium* bacterium for modulating palatability, maintaining body temperature, or protecting a blood vessel.

Another embodiment of the present invention is a method for modulating palatability, maintaining body temperature, or protecting a blood vessel by promoting the secretion of FGF21, the method including a step of administering a *Bifidobacterium* bacterium to a mammal or a step of administering the composition for promoting the secretion of FGF21 of the present invention to a mammal.

Another embodiment of the present invention is use of a *Bifidobacterium* bacterium for the manufacture of a pharmaceutical composition, a food or drink composition, or a feed composition for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation.

Another embodiment of the present invention is a *Bifidobacterium* bacterium used for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation.

Another embodiment of the present invention is use of a *Bifidobacterium* bacterium for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation.

Another embodiment of the present invention is a method for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation, the method including a step of administering a *Bifidobacterium* bacterium to a mammal or a step of administering the composition for promoting the secretion of FGF21 of the present invention to a mammal.

EXAMPLES

The present invention will be described more specifically below with respect to examples but the present invention is not to be limited to the examples.

Example 1

Effects of *Bifidobacterium breve* M-16V (NITE BP-02622) and lactulose, raffinose, and galactooligosaccharide on expression of FGF21 gene in liver and concentration of FGF21 in serum Bacterial cell powder ($2.4 \times 10^{11}$ cfu/g) of *Bifidobacterium breve* M-16V (NITE BP-02622) triturated with starch was suspended in physiological saline to prepare a *Bifidobacterium* liquid of $2.5 \times 10^9$ cfu/ml.

Lactulose (manufactured by Morinaga Milk Industry Co., Ltd.), raffinose (product name: Nitten Rraffinose, manufactured by Nippon Beet Sugar Manufacturing Co., Ltd.), and galactooligosaccharide were mixed at a ratio by weight of 1:1:1 and diluted in distilled water to prepare an oligosaccharide stock solution having a total final concentration of 250 mg/ml. The galactooligosaccharide is obtained by removing monosaccharides and disaccharides from a commercial product (product name: Oligomate 55N, manufactured by Yakult Pharmaceutical Industry Co., Ltd.) and contains about 65% by weight of Galβ1-4Galβ1-4Glc (4'-galactosyl lactose) and about 15% by weight of Galβ1-6Galβ1-4Glc (6'-galactosyl lactose).

The administration samples were physiological saline, a 5-fold diluted liquid of the *Bifidobacterium* liquid in physiological saline (final concentration of *Bifidobacterium*: 5×10$^8$ cfu/ml), a mixture of physiological saline and the oligosaccharide stock solution at 1:4 by volume (final concentration of oligosaccharide: 200 mg/ml), and a mixture of the *Bifidobacterium* liquid and the oligosaccharide stock solution at 1:4 by volume (final concentration of *Bifidobacterium*: 5×10$^8$cfu/ml, final concentration of oligosaccharide: 200 mg/ml).

Two-day-old C57BL/6J male mice and a mother mouse were purchased from Japan SLC Inc. The neonatal mice voluntarily took the breast milk of the mother mouse. At five days old, the neonatal mice were divided into four groups without variation in the body weight from one group to another.

A: Vehicle group (physiological saline was administered)

B: *Bifidobacterium* group (the diluted *Bifidobacterium* liquid was administered)

C: Oligosaccharide group (the oligosaccharide liquid was administered)

D: Oligosaccharide+*Bifidobacterium* group (The mixture liquid of oligosaccharide and *Bifidobacterium* was administered)

During 6 to 20 days old, 100 µl of the respective administration samples were administered to the neonatal mice of the respective groups once a day. Specifically, 5×10$^7$ cfu of the *Bifidobacterium breve* M-16V (NITE BP-02622) was administered to group B, 20 mg of oligosaccharide was administered to the group C, 20 mg of oligosaccharide and 5×10$^7$ cfu of *Bifidobacterium breve* M-16V (NITE BP-02622) were administered to the group D per one administration.

Each animal was subjected to anatomy at 21 days old and the serum and liver were taken out of the body. The FGF21 concentration in the serum and the expression of FGF21 gene in the liver were determined. The FGF21 concentration in the serum was measured with an ELISA kit (manufactured by R&D Systems). The expression of FGF21 gene in the liver was measured by RT-PCR. A primer of SEQ ID NO. 1 (CCTCTAGGTTTCTTTGCCAACAG) and a primer of SEQ ID NO. 2 (AAGCTGCAGGCCTCAGGAT) were used as a primer set in the RT-PCR. Tables 1 and 2 show the results.

TABLE 1

Expression of FGF21 gene in liver (values relative to the value of Group A which was taken as 100.0)

| Group | Average | Standard error |
|---|---|---|
| A | 100.0 | 32.7 |
| B | 197.7 | 64.1 |
| C | 121.6 | 37.8 |
| D | 266.7 | 68.6 |

TABLE 2

FGF21 Concentration in serum (pg/ml)

| | Average | Standard error |
|---|---|---|
| A | 378.2 | 75.6 |
| B | 397.3 | 66.0 |

TABLE 2-continued

FGF21 Concentration in serum (pg/ml)

| | Average | Standard error |
|---|---|---|
| C | 315.7 | 60.4 |
| D | 590.6 | 94.8 |

As shown in Table 1, at 21 days old, the expressions of FGF21 gene in the liver in the group B and the group D were significantly higher than those in the group A and the group C.

As shown in Table 2, the FGF21 concentration in the serum in the group D was significantly higher than those in the group A, group B, and group C.

Production Example 1

*Bifidobacterium breve* M-16V (NITE BP-02622) is added to 3 mL of an MRS liquid medium, and is anaerobically cultured at 37° C. for 16 hours, and then the culture liquid is concentrated, followed by lyophilization, to obtain a lyophilized powder of the bacterium (bacterial powder). The bacterial powder and a whey protein concentrate (WPC) are uniformly mixed to obtain a composition. 20 g of the composition is diluted in 200 g of water to obtain a composition for promoting the secretion of FGF21. By administering the composition, modulation of palatability, maintenance of body temperature, and protection of a blood vessel can be expected. Furthermore, the composition can be used for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation.

Production Example 2

*Bifidobacterium breve* M-16V (NITE BP-02622) is added to 3 mL of an MRS liquid medium and is anaerobically cultured at 37° C. for 16 hours and the culture liquid is concentrated, followed by lyophilization, to obtain a lyophilized powder of the bacterium (bacterial powder). The bacterial powder and a dry powder of a milk protein concentrate (MPC480, manufactured by Fonterra, protein content: 80% by mass, casein: whey protein=about 8:2) are uniformly mixed to obtain a composition. 20 g of the composition is diluted in 200 g of water to obtain a composition for promoting the secretion of FGF21. By administering the composition, modulation of palatability, maintenance of body temperature, and protection of a blood vessel can be expected. Furthermore, the composition can be used for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation.

Production Example 3

*Bifidobacterium breve* M-16V (NITE BP-02622) is added to 3 mL of an MRS liquid medium, and is anaerobically cultured at 37° C. for 16 hours, and the culture liquid is concentrated, followed by lyophilization, to obtain a lyophilized powder of the bacterium (bacterial powder). Next, crystalline cellulose is put in an agitation granulator and mixed. Then, purified water was added, followed by granulation. The granulated product is dried to obtain granules that contain an extracted component of the bacterium and an excipient. By administering the composition, modulation of palatability, maintenance of body temperature, and protection of a blood vessel can be expected. Furthermore, the composition can be used for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation.

Production Example 4

Bifidobacterium breve M-16V (NITE BP-02622) is added to 3 mL of an MRS liquid medium and is anaerobically cultured at 37° C. for 16 hours, and the culture liquid is concentrated, followed by lyophilization, to obtain a lyophilized powder of the bacterium (bacterial powder). The bacterial powder and a prebiotic (lactulose, raffinose, and galactooligosaccharide) are uniformly mixed to obtain a composition. The composition is provided to elderly persons as a liquid food for the aged. The composition is daily provided at breakfast for one week such an amount that the intake of the Bifidobacterium breve M-16V (NITE BP-02622) is $1\times10^8$ to $1\times101^{10}$ CFU/kg body/day. When Bifidobacterium breve M-16V (NITE BP-02622) is killed cells, CFU/kg body/day can be replaced by (individual cells)/kg body/day. Note that the composition may be mixed with a food or drink, such as a fermented milk. By orally administering the composition, modulation of palatability, maintenance of body temperature, and protection of a blood vessel can be expected. Furthermore, the composition can be used for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation.

Production Example 5

A method for producing a fermented milk with Bifidobacterium breve M-16V (NITE BP-02622) added thereto is shown below.

First, a milk raw material and water as needed, and other components are mixed, preferably followed by homogenization, and the mixture is then subjected to heat sterilization. The homogenization and heat sterilization can be performed by ordinary methods. A lactic acid bacterium starter is added (inoculated) to the heat-sterilized modified milk liquid, and is fermented while keeping a predetermined fermentation temperature to obtain a fermentation product. The fermentation causes formation of curd.

As the lactic acid bacterium starter, for example, a lactic acid bacterium that is typically used for production of a yogurt, such as Lactobacillus bulgaricus, Lactococcus lactis, or Streptococcus thermophilus, can be used. When the pH reaches a target value, the curd formed is broken by stirring and the resultant is cooled to 10° C. or lower to obtain a fermentation product. Cooling to 10° C. or lower allows for reduction of the activity of the lactic acid bacterium to suppress the acid production.

Next, the fermentation product obtained through the fermentation step is subjected to a heat treatment to obtain a fermentation product after heating (a fermentation product after the heat treatment). Appropriately heating the fermentation product allows for suppression of the acid production by the lactic acid bacterium in the fermentation product after heating. This can suppress a reduction in the pH during the subsequent production steps and/or during the storage of the concentrated fermented milk with Bifidobacterium, resulting in an increase in the viability of the Bifidobacterium.

Next, Bifidobacterium breve M-16V (NITE BP-02622) is added to the fermentation product after heating obtained by the heat treatment step. The amount of the Bifidobacterium breve M-16V (NITE BP-02622) added is preferably $1\times10^7$ to $1\times10^{11}$ CFU/ml based on the fermentation product after heating, and more preferably $1\times10^8$ to $1\times10^{10}$ CFU/ml. When Bifidobacterium breve M-16V (NITE BP-02622) is killed cells, CFU/ml can be replaced by (individual cells)/ml.

The addition of the Bifidobacterium breve M-16V (NITE BP-02622) to the fermentation product after heating is followed by concentration. The concentration step can be performed appropriately using a known concentration method. For example, a centrifugal separation method or a membrane separation method can be used.

In a centrifugal separation method, whey in the object to be concentrated (the fermentation product after heating with Bifidobacterium added thereto) is removed and a concentrated fermented milk with Bifidobacterium that has an increased solid concentration can be obtained.

By taking the fermented milk obtained as described above, modulation of palatability, maintenance of body temperature, and protection of a blood vessel can be expected. Furthermore, the fermented milk can be used for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation.

Production Example 6

A method for producing a powdered infant formula with Bifidobacterium breve M-16V (NITE BP-02622) added thereto is described below.

10 kg of a demineralized milk whey protein powder (manufactured by Milei GmbH), 6 kg of a milk casein powder (manufactured by Fonterra), 48 kg of lactose (manufactured by Milei GmbH), 920 g of a mineral mixture (manufactured by Tomita Pharmaceutical Co., Ltd.), 32 g of a vitamin mixture (manufactured by Tanabe Seiyaku Co., Ltd.), 500 g of lactulose (manufactured by Morinaga Milk Industry Co., Ltd.), 500 g of raffinose (manufactured by Nippon Beet Sugar Manufacturing Co., Ltd.), and 900 g of galactooligosaccharide syrup (manufactured by Yakult Pharmaceutical Industry Co., Ltd.) are diluted in 300 kg of hot water, and are further diluted with heat at 90° C. for 10 minutes, and then 28 kg of a modified fat (manufactured by TAIYO YUSHI) is added, followed by homogenization. Then, steps of sterilization and concentration are performed and the resultant is spray-dried to prepare about 95 kg of a powdered infant formula. To the powdered infant formula, 100 g of a bacterial cell powder ($1.8\times10^{11}$ cfu/g, manufactured by Morinaga Milk Industry Co., Ltd.) of Bifidobacterium breve M-16V (NITE BP-02622) triturated with starch is added to prepare about 95 kg of a powdered infant formula with Bifidobacterium and oligosaccharide. When the resulting powdered infant formula is dissolved in water to produce a liquid infant formula having a total solid concentration, which is a standard infant formula concentration, of 14% (w/V), the number of cells of the Bifidobacterium in the liquid infant formula is $2.7\times10^9$ cfu/100 ml. By taking the powdered infant formula obtained as described above, modulation of palatability, maintenance of body temperature, and protection of a blood vessel can be expected. Furthermore, the powdered infant formula can be used for preventing or treating unbalanced diet, sensitivity to cold, hypothermia, myocardial infarction, ischemia-reperfusion injury, cardiac hypertrophy, diabetic cardiomyopathy, arteriosclerosis, or vascular plaque formation.

The invention claimed is:

1. A method for modulating palatability in a subject in need of said modulating, comprising administering a *Bifidobacterium* bacterium in an effective amount for modulating palatability to said subject,
   wherein the *Bifidobacterium* bacterium is *Bifidobacterium breve* M-16V (NITE BP-02622),
   wherein said modulating occurs via promotion of secretion of FGF21 in said subject, and
   wherein modulating palatability is reducing the unbalanced types of diet, helping to take a wide variety of types of diet without faddiness, and adjusting the sense of taste.

2. The method according to claim 1, wherein the *Bifidobacterium* bacterium is comprised in a food or drink composition.

3. The method according to claim 1, wherein the *Bifidobacterium* bacterium is comprised in a pharmaceutical composition.

4. A method for maintaining body temperature in a subject in need of said maintaining, comprising administering a *Bifidobacterium* bacterium in an effective amount for maintaining body temperature to said subject,
   wherein the *Bifidobacterium* bacterium is *Bifidobacterium breve* M-16V (NITE BP-02622), and
   wherein said maintaining occurs via promotion of secretion of FGF21 in said subject.

5. The method according to claim 4, wherein the *Bifidobacterium* bacterium is comprised in a food or drink composition.

6. The method according to claim 4, wherein the *Bifidobacterium* bacterium is comprised in a pharmaceutical composition.

7. A method of improving a sensitivity to cold in a subject in need of said improving, comprising administering a *Bifidobacterium* bacterium in an effective amount for improving the sensitivity cold, wherein the *Bifidobacterium* bacterium is *Bifidobacterium breve* M-16V (NITE BP-02622), and
   wherein said improving occurs via promotion of the secretion of FGF21 in said subject.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: primer 1

<400> SEQUENCE: 1
cctctaggtt tctttgccaa cag        23

<210> SEQ ID NO 2
<211> LENGTH: 19
<212> TYPE: DNA
<213> ORGANISM: Artificial Sequence
<220> FEATURE:
<223> OTHER INFORMATION: primer 2

<400> SEQUENCE: 2
aagctgcagg cctcaggat        19